United States Patent [19]

Sutherland et al.

[11] Patent Number: 4,900,753
[45] Date of Patent: Feb. 13, 1990

[54] MACROLIDE COMPOUNDS

[75] Inventors: Derek R. Sutherland, Chalfont St. Giles; Michael V. J. Ramsay, South Harrow; Edward P. Tiley, Village Way; Oswy Z. Pereira, Heston; John B. Ward, Bushey; Neil Porter, Pinner; Hazel M. Noble, Burnham; Richard A. Fletton, Ruislip; David Noble, Burnham, all of England

[73] Assignee: American Cyanamid Company, Stamford, Conn.

[21] Appl. No.: 58,856

[22] Filed: Jun. 5, 1987

[30] Foreign Application Priority Data

Jun. 6, 1986 [GB] United Kingdom ............... 8613790
Oct. 29, 1986 [GB] United Kingdom ............... 8625854
Apr. 8, 1987 [GB] United Kingdom ............... 8708423

[51] Int. Cl.[4] .................. A61K 31/335; C07D 313/06
[52] U.S. Cl. ..................................... 514/450; 549/264
[58] Field of Search ..................... 549/264; 514/450

[56] References Cited

U.S. PATENT DOCUMENTS 4,423,209 12/1983 Mrozik ............................. 549/264
4,547,520 10/1985 Ide et al. ......................... 549/264
4,579,864 4/1986 Linn et al. ....................... 549/264

FOREIGN PATENT DOCUMENTS 142969 5/1985 European Pat. Off. .
170006 2/1986 European Pat. Off. .

Primary Examiner—Glennon H. Hollrah
Assistant Examiner—Ba K. Trinh
Attorney, Agent, or Firm—Bacon & Thomas

[57] ABSTRACT

Compounds are described of formula (I)

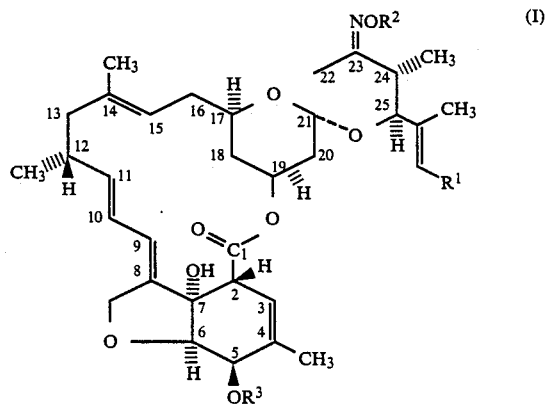

and salts thereof, wherein $R^1$ represents a methyl, ethyl or isopropyl group;

$R^2$ represents a hydrogen atom, a $C_{1-8}$ alkyl group or a $C_{3-8}$ alkenyl group and the group $=NOR^2$ is in the E-configuration;

$OR^3$ is a hydroxyl group or a substituted hydroxyl group having up to 25 carbon atoms.

These compounds may be used for controlling insect, acarine, nematode or other pests.

13 Claims, No Drawings

MACROLIDE COMPOUNDS

This invention relates to novel antibiotic compounds, to processes for their preparation and to pharmaceutical compositions containing them.

In our United Kingdom Patent Specification 2166436 we describe the production of Antibiotics S541 which may be isolated from the fermentation products of a novel Streptomyces sp. Said antibiotic compound can also be produced by fermentation of microorganism Streptomyces ssp. deposited in the Northern Regional Research Center under Accession No. NRRL 15773 as disclosed in U.S. Ser. No. 617,649, filed June 5, 1984, now U.S. Pat. No. 4,869,901.

We have now found a further group of compounds with antibiotic activity which may be prepared by chemical modification of Antibiotics S541.

Thus, in one aspect, the invention particularly provides the compounds of formula (I)

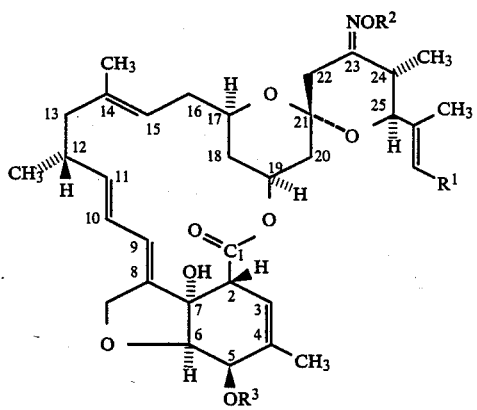

and salts thereof, wherein $R^1$ represents a methyl, ethyl or isopropyl group; $R^2$ represents a hydrogen atom, a $C_{1-8}$ alkyl group or a $C_{3-8}$ alkenyl group; $OR^3$ is a hydroxyl group or a substituted hydroxyl group having up to 25 carbon atoms; and the group $=NOR^2$ is in the E configuration.

The term 'alkyl' or 'alkenyl' as a group or part of a group in the compounds of formula (I) means that the group is straight or branched.

When $R^2$ in the compounds of formula (I) is a $C_{1-8}$ alkyl group, it may be for example a methyl, ethyl, n-propyl, i-propyl, n-butyl, i-butyl or t-butyl group, and is preferably a methyl group.

When $R^2$ is a $C_{3-8}$ alkenyl group, it may be for example an allyl group.

When the group $OR^3$ in compounds of formula (I) is a substituted hydroxyl group it may represent an acyloxy group [e.g. a group of the formula $-OCOR^4$, $-OCO_2R^4$ or $-OCSOR^4$ (where $R^4$ is an aliphatic, araliphatic or aromatic group, for example an alkyl, alkenyl, alkynyl, cycloalkyl, aralkyl or aryl group)], a formyloxy group, a group $-OR^5$ (where $R^5$ is as defined above for $R^4$), a group $-OSO_2R^6$ (where $R^6$ is a $C_{1-4}$ alkyl or $C_{6-10}$ aryl group), a cyclic or acyclic acetaloxy group, a group $OCO(CH_2)_nCO_2R^7$ (where $R^7$ is a hydrogen atom or a group as defined for $R^4$ above and n represents zero, 1 or 2) or a group $OCONR^8R^9$ (where $R^8$ and $R^9$ may each independently represent a hydrogen atom or a $C_{1-4}$ alkyl group e.g. methyl).

Where $R^4$ or $R^5$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^4$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^5$ is a substituted alkyl group it may be substituted by a cycloalkyl e.g. cyclopropyl group.

Where $R^4$ or $R^5$ are alkenyl or alkynyl groups, they may be for example $C_{2-8}$ alkenyl, e.g. allyl, or $C_{2-8}$ alkynyl groups.

Where $R^4$ or $R^5$ are cycloalkyl groups, they may be for example $C_{3-12}$ cycloalkyl, such as $C_{3-7}$ cycloalkyl, e.g. cyclopentyl groups.

Where $R^4$ or $R^5$ are aralkyl groups, they preferably have 1 to 6 carbon atoms in the alkyl moiety and the aryl group(s) may be carbocyclic or heterocyclic and preferably contain 4–15 carbon atoms e.g. phenyl. Examples of such groups include $phenC_{1-6}alkyl$, e.g. benzyl groups.

Where $R^4$ or $R^5$ are aryl groups, they may be carbocyclic or heterocyclic and preferably have 4–15 carbon atoms, and may be for example a phenyl group.

When $R^4$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^4$ and particularly include methyl, t-butyl and phenyl groups. Particular examples of such silyloxy groups are trimethylsilyloxy and t-butyldimethylsilyloxy.

When $-OR^3$ is a group $-OSO_2R^6$, it may be for example a methylsulphonyloxy or p-toluenesulphonyloxy group.

Where $-OR^3$ represents a cyclic acetaloxy group, it may for example have 5–7 ring members and may be for example a tetrahydropyranyloxy group.

Where $OR^3$ represents a group $OCO(CH_2)_nCO_2R^7$, it may for example be a group $OCOCO_2R^{7a}$ or $OCOCH_2CH_2CO_2R^{7a}$ where $R^{7a}$ represents a hydrogen atom or a $C_{1-4}$ alkyl (e.g. methyl or ethyl) group.

Salts that may be formed with compounds of formula (I) containing an acidic group include salts with bases e.g. alkali metal salts such as sodium and potassium salts.

In the compounds of formula (I), the group $R^1$ is preferably an isopropyl group.

The group $OR^3$ is preferably a methoxycarbonyloxy, or, especially, an acetoxy, methoxy or hydroxy group. In general, compounds of formula (I) in which $OR^3$ is a hydroxy group are particularly preferred.

Important compounds according to the invention are those of formula (I) in which $R^1$ is an isopropyl group, $R^2$ is a methyl group and $OR^3$ is a hydroxy, acetoxy, or methoxycarbonyloxy group.

As indicated previously, the compounds according to the invention may be of use as antibiotics. The compounds of the invention may also be of use as intermediates for the preparation of other active compounds. When the compounds of the invention are to be used as intermediates, the $-OR^3$ groups may be a protected hydroxyl group and the invention particularly includes such protected compounds. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Greene. (Wiley-Interscience, New York 1981) and "Protective Groups in Organic Chemistry" by J F W McOmie (Plenum Press, London, 1973). Examples of $OR^3$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparastic activity.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Cyathostomes, Dictyocaulus, Dirofilaria, Dracunculus, Enterobius, Gastrophilus, Haemonchus, Heterakis, Hyostrongylus, Loa, Metastrongylus, Necator, Nematodirus, Nematospiroides, Nippostrongylus, Oesophagostomum, Onchocerca, Ostertagia, Oxyuris, Parafilaria, Parascaris, Probstmayria, Strongylus, Strongyloides, Syphacia, Thelazia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Anopheles, Boophilus, Chorioptes, Culexpipiens, Culliphore, Demodex, Damalinia, Dermatobia, Haematobia, Haematopinus, Haemophysalis, Hyaloma, Hypoderma, Ixodes, Linognathus, Lucillia, Melophagus, Oestrus, Otobius, Otodectes, Psorergates, Psoroptes, Rhipicephalus, Sarcoptes, Solenopotes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabditis elegans* and *Nematospiroides dubius*.

An important active compound of the invention is that of formula (I) in which:

$R^1$ is a methyl group, $R^2$ is a methyl group and $OR^3$ is a methoxy group.

Another important active compound of the invention is that of formula (I) in which:

$R^1$ is an ethyl group, $R^2$ is a methyl group and $OR^3$ is a hydroxyl group.

A particularly important active compound of the invention is that of formula (I) in which:

$R^1$ is an isopropyl group, $R^2$ is a methyl group and $OR^3$ is a hydroxyl group.

The compound of formula (I) in which $R^1$ is an isopropyl group, $R^2$ is a methyl group and $OR^3$ is a hydroxyl group is active against a wide range of endoparasites and ectoparasites. For example, this compound has been found to be active in vivo against parasitic nematodes such as Ascaris, *Cooperia curticei, Cooperia oncophora*, Cyathostomes, *Dictyocaulus viviparus, Dirofilaria immitis*, Gastrophilus, *Haemonchus contortus, Nematodirus battus, Nematodirus helvetianus, Nematodirus spathiger, Nematospiroides dubius, Nippostrongylus braziliensis*, Oesophaostomum, *Onchocera gutturosa, Ostertagia circumcincta, Ostertagia ostertagi, Oxyuris equi, Parascaris equorum*, Probstmayria, *Strongylus edentatus, Strongylus vulgaris, Toxocara canis, Trichostrongylus axei, Trichostrongylus vitrinus, Triodontophorus* and *Uncinaria stenocephala*, and parasitic grubs, mange mites, ticks and lice such as *Amblyomma hebraeum, Anopheles stevensi, Boophilus dicolarartus, Boophilus microplus, Chorioptes ovis, Culexpipiens molestus, Damalinia bovis*, Dermatobia, Haematopinus, Hypoderma, *Linognathus vituli, Lucilia sericata, Psoroptes ovis, Rhipicephalus appendiculatus* and Sarcoptes.

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius;* flour beetles such as *Tribolium castaneum;* flies such as *Musca domestica;* fire ants; leaf miners; *Pear psylla; Thrips tabaci;* cockroaches such as *Blatella germanica* and *Periplaneta americana* and mosquitoes such as *Aedes aegypti*.

In particular, we have found that the compound of formula (I) in which $R^1$ is an isopropyl group, $R^2$ is a methyl group and $OR^3$ is a hydroxyl group is active against *Tetranychus urticae* (supported on french bean leaf), *Myzus persicae* (supported on chinese cabbage leaf), *Heliothis virescens* (supported on cotton leaf), *Nilaparvata lugens* (supported on rice plant), *Musca domestica* (in a plastic pot with cotton wool/sugar solution), *Blattella germanica* (in a plastic pot with food pellets), *Spodoptera exigua* (supported on a cotton leaf) and *Meloidogyne incognita*.

Compounds of the invention may also be of use as anti-fungals, for example, against strains of Candida sp. such as *Candida albicans* and *Candida glabrata* and against yeast such as *Saccharomyces carlsbergensis*.

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, intraruminal, implant, ophthalmic, nasal or genito-urinary use.

The compounds according to the invention may be formulated for use in veterinary or human medicine by injection and may be presented in unit dose form, in ampoules, or other unit-dose containers, or in multi-dose containers, if necessary with an added preservative. The compositions for injection may be in the form of suspensions, solutions, or emulsions, in non-aqueous or aqueous vehicles, and may contain formulatory agents such as suspending, stabilising, emulsifying, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil, cottonseed oil or fractionated coconut oil, mineral oils such as liquid paraffin, isopropyl myristate and ethyl oleate and other similar compounds. Other vehicles containing materials such as glycerol formal, propylene glycol, polyethylene glycols, ethanol or glycofurol may also be used. Conventional non-ionic, cationic or anionic surface active agents may be used alone or in combination in the composition.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups, emulsions or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be included.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates; non-aqueous vehicles e.g. arachis oil, oily esters, glycols or macrogols; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically aceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in organic solvents or as an aqueous suspension, and may include agents which promote percutaneous adsorption, and formulation agents which solubilise, stabilise, preserve or otherwise improve the storage properties and/or ease of application.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For administration by inhalation the compounds according to the invention may be delivered for use in veterinary or human medicine in the form of an aerosol spray presentation or an insufflator.

The total daily dosages of compounds of the invention employed in both veterinary and human medicine will suitably be in the range 1–2000 μg/kg bodyweight, preferably from 5–800 μg/kg and these may be given in divided doses, e.g. 1–4 times per day. It will be appreciated that the dosage will vary according to the age and condition of the patient, the organism being treated, the mode of administration and the particular composition formulated. Dosages for a given host can be determined using conventional considerations, eg. by comparison of the activities of the subject compound and of a known antibiotic agent.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-forming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The rate at which a compound is applied depends upon a number of factors including the type of pest involved and the degree of infestation. However, in general, an application rate of 10 g/ha to 10 kg/ha will be suitable; preferably from 10 g/ha to 1 kg/ha for control of mites and insects and form 50 g/ha to 10 kg/ha for control of nematodes.

The compounds of the invention may be administered or used in combination with other active ingredients. In particular, the compounds of the invention may be administered or used in combination with other known anthelmintic agents. By combining the compounds of the invention with other anthelmintic agents the spectrum of parasitic infections which may be successfully combatted may be expanded. Thus, the possibility of eliminating parasitic infections against which the individual components are ineffective or only partially effective may be realised.

The compounds of the invention may be prepared by the processes discussed below. In some of these processes it may be necessary to protect a hydroxyl group at the 5-position in the starting material prior to effecting the reaction described. In such cases it may then be necessary to deprotect the same hydroxyl group once the reaction has occurred to obtain the desired compound of the invention. Conventional protection and deprotection methods may be used, for example as described in the aforementioned books by Greene and McOmie.

According to one aspect of the invention we provide a process (A) for the preparation of compounds of formula (I) which comprises reacting compounds of formula (II):

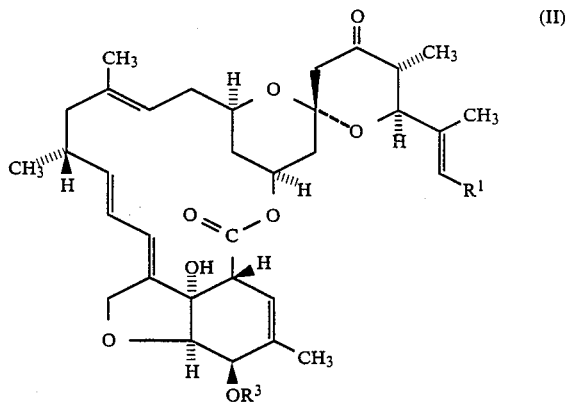

(II)

(where $R^1$ and $OR^3$ are as previously defined) with a reagent $H_2NOR^2$ or a salt thereof (where $R^2$ is as previously defined), and, if desired, followed by deprotection of a compound of formula (I) in which $OR^3$ is a protected hydroxyl group, and optionally followed by salt formation.

The oximation reaction may be effected in aqueous or non-aqueous reaction media, conveniently at a temperature in the range $-20°$ to $+100°$ C., e.g. $-10°$ to $+50°$ C. It is convenient to use the reagent $H_2NOR^2$ in the form of a salt, for example an acid addition salt such as the hydrochloride. When such a salt is employed the reaction may be carried out in the presence of an acid binding agent.

Solvents which may be employed include water and water miscible solvents such as alcohols (e.g. methanol or ethanol), amides (e.g. N,N-dimethylformamide, N,N-dimethylacetamide or hexamethylphosphoramide), ethers (e.g. cyclic ethers such as tetrahydrofuran or dioxan, and acylic ethers such as dimethoxyethane or diethylether), nitriles (e.g. acetonitrile), sulphones (e.g. sulpholane), hydrocarbons such as halogenated hydrocarbons (e.g. methylene chloride), and esters such as ethyl acetate, as well as mixtures of two or more such solvents.

When aqueous conditions are employed the reaction may conveniently be buffered to pH 2–9 with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

Compounds of formula (II) are either known compounds described in UK Patent Specification 2176182 or may be prepared from known compounds described therein using standard procedures.

According to a further aspect of the invention we provide a further process (B) for the preparation of compounds of formula (I) in which $R^2$ is a $C_{1-8}$ alkyl or $C_{3-8}$ alkenyl group and $OR^3$ is a substituted hydroxyl group which comprises reacting a compound of formula (I) in which $OR^3$ is a hydroxyl group with a reagent serving to convert a hydroxyl group into a substituted hydroxyl group, optionally followed by salt formation.

Acylation, formylation, sulphonylation, etherification, silylation or acetal formation reactions may be carried out by conventional methods as described below.

Thus, for example, acylation may be effected using an acylating agent such as an acid of formula $R^4COOH$ or a reactive derivative thereof, such as an acid halide (e.g. acid chloride), anhydride or activated ester, or a reactive derivative of a carbonic acid $R^4OCOOH$ or thiocarbonic acid $R^4OCSOH$.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range $-20°$ to $+100°$ C., e.g. $-10°$ to $+50°$ C.

Formylation may be effected using an activated derivative of formic acid e.g. N-formyl imidazole or formic acetic anhydride under standard reaction conditions.

Sulphonylation may be effected with a reactive derivative of a sulphonic acid $R^6SO_3H$ such as a sulphonyl halide, for example a chloride $R^6SO_2Cl$ or a sulphonic anhydride. The sulphonylation is preferably effected in the presence of a suitable acid binding agent as described above.

Etherification may be effected using a reagent of formula $R^5Y$ (where $R^5$ is as previously defined and Y represents a leaving group such as chlorine, bromine or iodine atom or a hydrocarbylsulphonyloxy group, such as mesyloxy or tosyloxy, or a haloalkanoyloxy group such as dichloroacetoxy). The reaction may be carried out by formation of a magnesium alkoxide using a Grignard reagent such as methylmagnesium halide e.g. methylmagnesium iodide or using a trialkylsilylmethylmagnesium halide e.g. trimethylsilylmethylmagnesium chloride followed by treatment with the reagent $R^5Y$.

Alternatively, the reaction may be effected in the presence of a silver salt such as silver oxide, silver perchlorate, silver carbonate or silver salicylate or mixtures thereof, and this system may be particularly appropriate when etherification is carried out using an alkyl halide (e.g. methyl iodide).

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Solvents which may be employed in the above reactions include ketones (e.g. acetone), amides (e.g. N,N-dimethylformamide, N,N-dimethylacetamide or hexamethylphosporamide), ethers (e.g. cyclic ethers such as tetrahydrofuran or dioxan, and acyclic ethers such as dimethoxyethane or diethylether), nitriles (e.g. acetonitrile), hydrocarbons such as halogenated hydrocarbons (e.g. methylene chloride), and esters such as ethyl acetate, as well as mixtures of two or more such solvents.

Silylation may be effected by reaction with a silyl halide (e.g. chloride), advantageously in the presence of a base such as imidazole triethylamine or pyridine, using a solvent such as dimethylformamide.

Carbamoylation to provide a compound of formula (I) in which $OR^3$ is a group $OCONR^8R^9$ may be effected by reaction with a suitable acylating (ie carbamoylating) agent. Suitable carbamoylating agents which may be used to afford compounds in which one of $R^8$ and $R^9$ is a hydrogen atom and the other is a $C_{1-4}$ alkyl group include isocyanates of formula $R^{10}NCO$ (wherein $R^{10}$ is a $C_{1-4}$ alkyl group). The carbamoylation reaction may desirably be effected in the presence of a solvent or solvent mixture selected from hydrocarbons (e.g. aromatic hydrocarbons such as benzene and toluene), halogenated hydrocarbons (e.g. dichloromethane), amides (e.g. formamide or dimethylformamide), esters (e.g. ethyl acetate), ethers (e.g. cyclic ethers such as tetrahydrofuran and dioxan), ketones (e.g. acetone), sulphoxides (e.g. dimethylsulphoxide) or mixtures of these solvents. The reaction may conveniently be carried out at a temperature of between −80° C. and the boiling temperature of the reaction mixture, for example up to 100° C., preferably between −20° and +30° C.

The carbamoylation may be assisted by the presence of a base, e.g. a tertiary organic base such as tri-(lower alkyl)amine (e.g. triethylamine).

Another useful carbamoylating agent is cyanic acid, which is conveniently generated in situ, for example, from an alkali metal cyanate such as sodium cyanate, the reaction being facilitated by the presence of an acid, e.g. a strong organic acid such as trifluoroacetic acid. Cyanic acid effectively corresponds to the isocyanate compounds mentioned above wherein $R^{10}$ is hydrogen and therefore converts compounds of formula (II) directly to their carbamoyloxy analogues (i.e. compounds of formula (I) in which $OR^3$ is a group $OCONH_2$).

Alternatively, carbamoylation may be effected by reaction with phosgene or carbonylidiimidazole followed by ammonia or the appropriate substituted amine, optionally in an aqueous or non-aqueous reaction medium.

The formation of compounds of formula (I) in which $OR^3$ represents a group $OCO(CH_2)_nCO_2R^7$ may be achieved by acylation of the corresponding 5-hydroxy compound with an acid $HO_2C(CH_2)_nCO_2R^7$ or a reactive derivative thereof according to the acylation procedure described above.

According to another aspect of the invention we provide a further process (C) for the preparation of compounds of formula (I) in which $R^2$ is a $C_{1-8}$ alkyl or $C_{3-8}$ alkenyl group which comprises reacting a compound of formula (I) in which $R^2$ is a hydrogen atom and $OR^3$ is a substituted hydroxyl group with an etherifying agent $R^2Y$ (where $R^2$ is a $C_{1-8}$ alkyl or $C_{3-8}$ alkenyl group and Y is as previously defined), and if desired followed by deprotection of a compound of formula (I) in which $OR^3$ is a protected hydroxyl group, and optionally followed by salt formation.

The etherification reaction may be carried out, for example, by formation of a magnesium alkoxide using a Grignard reagent such as a methylmagnesium halide e.g. methylmagnesium iodide followed by treatment with the reagent $R^2Y$. Alternatively, the reaction may be effected in the presence of a silver salt such as silver oxide, silver perchlorate, silver carbonate or silver salicylate or mixtures thereof or in the presence of a base e.g. potassium carbonate or sodium hydride. Etherification may conveniently be carried out in an organic solvent such as an ether e.g. diethyl ether, tetrahydrofuran or dioxan or an amide e.g. dimethylformamide or hexamethylphosphoric triamide or a mixture of such solvent at ambient temperature. Under these conditions the configuration of the oximino group is substantially unchanged by the etherification reaction.

According to another aspect of the invention we provide a yet further process (D) for the preparation of compounds of formula (I) in which $OR^3$ is a hydroxyl group which comprises reducing a compound of formula (III)

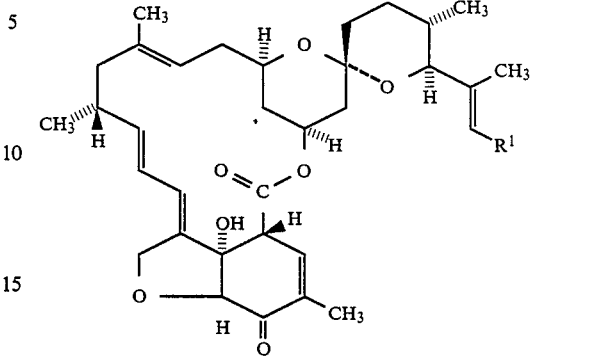

and optionally followed by salt formation.

The reduction may be effected with a reducing agent which is capable of stereoselectively reducing the 5-keto group. Suitable reducing agents include borohydrides such as alkali metal borohydrides (e.g. sodium borohydride) and lithium alkoxyaluminium hydrides such as lithium tributoxyaluminium hydride.

The reaction involving a borohydride reducing agent takes place in the presence of a solvent such as an alkanol e.g. isopropyl alcohol or isobutyl alcohol conveniently at a temperature in the range of −30° to +80° C. e.g. at 0° C. The reaction involving a lithium alkoxyaluminium hydride takes place in the presence of a solvent such as an ether e.g. tetrahydrofuran or dioxan conveniently at a temperature in the range of −78° to 0° C.

Intermediate compounds of formula (III) may be prepared from a 5,23-diketone of formula (IV)

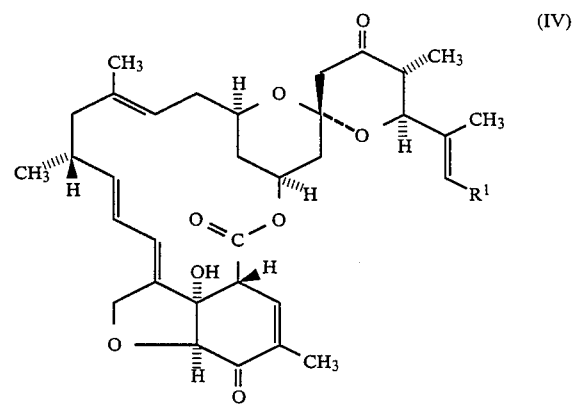

by treatment with one equivalent of a reagent $H_2NOR^2$ (where $R^2$ is as previously defined) using the oximation conditions described above for the preparation of compounds of formula (I).

Compounds of formula (IV) may be prepared by oxidising a compound of formula (V)

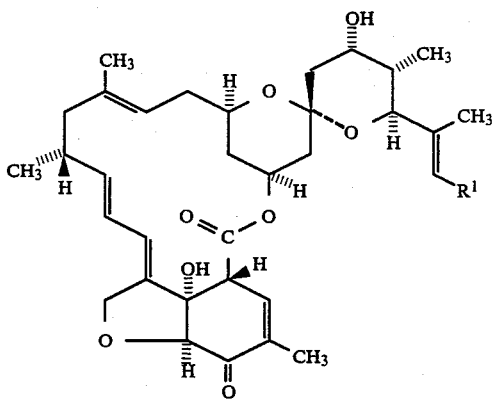

(V)

The reaction may be effected with an oxidising agent serving to convert a secondary hydroxyl group to an oxo group, whereby a compound of formula (IV) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. sodium or pyridinium dichromate or chromium trioxide in pyridine preferably in the presence of a phase transfer catalyst; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicylcohexylcarbodiimide or an acyl halide, e.g. oxalyl chloride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used. The choice of solvent will depend upon the type of oxidising agent used for the conversion.

The reaction may be carried out at a temperature of from $-80°$ C. to $+50°$ C.

The compounds of formula (V) may be prepared, for example, by cultivating *Streptomyces thermoarchaensis* NCIB 12015 (deposited 10th Sept. 1984 in the permanent culture collection of the National Collections of Industrial and Marine Bacteria, Torry Research Station, Aberdeen, United Kingdom) or a mutant thereof and isolating the compound from the fermentation broth so obtained.

The Streptomyces organism may be cultured by conventional means, i.e. in the presence of assimilable sources of carbon, nitrogen and mineral salts. Assimilable sources of carbon, nitrogen and minerals may be provided by either simple or complex nutrients for example as described in UK Patent Specification 2166436. Suitable media comprising these are described in Preparation 1 hereinafter.

Cultivation of the Streptomyces organism will generally be effected at a temperature of from 20° to 50° C. preferably from 25° to 40° C., and will desirably take place with aeration and agitation e.g. by shaking or stirring. The medium may initially be inoculated with a small quantity of a sporulated suspension of the microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 5.5 to 8.5.

The fermentation may be carried out for a period of 2-10 days, e.g. about 5 days.

The compounds of formula (V) may be separated from the whole fermentation broth so obtained by conventional isolation and separation techniques. A variety of fractionation techniques may be used, for example adsorption-elution, precipitation, fractional crystallisation and solvent extraction which may be combined in various ways. Solvent extraction and chromatography have been found to be most suitable for isolating and separating the compound. A suitable method for obtaining the compounds of formula (V) using these procedures is described in Preparation 1 hereinafter.

According to another aspect of the invention we provide a further process (E) for the preparation of compounds of formula (I) in which $OR^3$ is a hydroxyl group which comprises deprotecting a corresponding compound of formula (I) in which $OR^3$ is a protected hydroxyl group as described above.

Thus, for example, an acyl group such as an acetyl group may be removed by basic hydrolysis e.g. using sodium or potassium hydroxide in aqueous alcohol or by acid hydrolysis e.g. using concentrated sulphuric acid in methanol. Acetal groups such as tetrahydropyranyl may be removed for example, using acid hydrolysis (using an acid such as acetic or trifluoroacetic acid or a dilute mineral acid). Silyl groups may be removed using fluoride ions (e.g. from a tetraalkylammonium fluoride such as tetra-n-butylammonium fluoride), hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the the presence of a thiol (e.g. ethanethiol) in a suitable solvent such as dichloromethane at e.g. room temperature.

Salts of acids of formula (I) may be prepared by conventional methods, for example by treating the acid with a base or converting one salt into another by exchange of ion.

The invention is illustrated but not limited by the following Preparations and Examples in which temperatures are in °C., 'L' represents liter and EtOH represents ethanol.

In the following Preparations and Examples compounds are named as derivatives of the known 'Factors', Factors A, B, C and D. Factor A is a compound of formula (VI) in which $R^1$ is isopropyl and $R^3$ is hydrogen; Factor B is a compound of formula (VI) in which $R^1$ is methyl and $R^3$ is methyl; Factor C is a compound of formula (VI) in which $R^1$ is methyl and $R^3$ is hydrogen; and Factor D is a compound of formula (VI) in which $R^1$ is ethyl and $R^3$ is hydrogen.

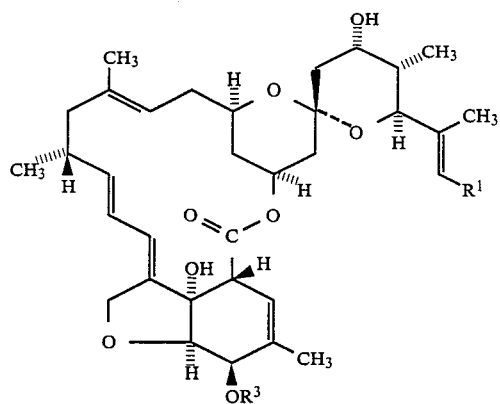

(VI)

Preparation 1—5-Keto Factor A

Spores of *Streptomyces thermoarchaensis* NCIB 12015 were inoculated onto agar slants made up of the following ingredients

|  | $gL^{-1}$ |
| --- | --- |
| Yeast extract (Oxoid L21) | 0.5 |
| Malt extract (Oxoid L39) | 30.0 |
| Mycological peptone (Oxoid L40) | 5.0 |
| Agar No. 3 (Oxoid L13) | 15.0 |
| Distilled water to 1 L | |
| pH ~ 5.4 | | and incubated at 28° for 10 days.

The mature slant was then covered with 6 ml of a 10% glycerol solution and scraped with a sterile tool to loosen the spores and mycelium. 0.4 ml aliquots of the resulting spore suspension were transferred to sterile polypropylene straws which were then heat-sealed and stored in liquid nitrogen vapour until required.

Two 250 ml Erlenmeyer flasks containing 50 ml of seed medium made up as follows:

|  | $gL^{-l}$ |
| --- | --- |
| D-Glucose | 15.0 |
| Glycerol | 15.0 |
| Soya peptone | 15.0 |
| NaCl | 3.0 |
| CaCO₃ | 1.0 |
| Distilled water to 1 L | |

[The unadjusted pH of the medium was 6.7 which was adjusted to pH 7.0 with aqueous sodium hydroxide before autoclaving. The pH of the medium after autoclaving was 7.3]

were each inoculated with 0.2 ml of the spore suspension taken from a straw.

The flasks were incubated at 28° for 3 days on a shaker rotating at 250 rpm with a 50 mm diameter orbital motion.

The contents of both flasks were used to inoculate a 70 L fermenter vessel containing 40 L of the same medium supplemented with polypropylene 2000 (0.06% v/v). Polypropylene 2000 was added as required throughout the fermentation to control foaming. The fermentation was carried out at 28°, with agitation and aeration sufficient to maintain a dissolved oxygen level of greater than 30% saturation. After 24 h of fermentation, a 9 L portion of broth was transferred to a 700 L fermenter containing 450 L of medium made up as follows:

|  | $gL^{-l}$ |
| --- | --- |
| D-glucose | 2.8 |
| Malt Dextrin (MD3OE) | 27.8 |
| Arkasoy 50 | 13.9 |
| Molasses | 1.7 |
| K₂HPO₄ | 0.14 |
| CaCO₃ | 1.39 |
| Silicone 525 (Dow Corning) | 0.06% (v,v) |

Adjusted to pH 6.5 before sterilization

The fermentation was carried out at 28° with agitation and aeration. Polypropylene 2000 antifoam was added as required and the pH was kept down to pH 7.2 by the addition of H₂SO₄ until harvest. The fermentation was harvested after 5 days.

The broth (450 L) was clarified on a Westfalia KA 25 centrifuge and the residual supernatant was displaced with water (20 L). The recovered cells (25.5 kg) were stirred for 1 h with a Silverson mixer model BX in sufficient methanol to give a total volume of 75 L. The suspension was filtered and the solid residue was re-extracted with methanol (35 L) and filtered. The combined filtrate (87 L) was diluted with water (40 L) and extracted with 60°–80° petroleum ether (30 L). After 30 min. the phases were separated on a Westfalia MEM 1256 centrifuge and the lower methanol phase was re-extracted with 60°–80° petroleum ether (30 L) after the addition of water (40 L). After separation the lower phase was again extracted with 60°–80° petroleum ether (30 L). The combined petroleum ether phases (85 L) were concentrated by three passes through a Pfaudler 8.8-12v-27 wiped-film evaporator (vapour pressure 0.1 bar, vapour temperature 20°, steam temperature 127°). The concentrate (9 L) was dried with sodium sulphate (2 kg) and further concentrated under reduced pressure at 40° in a rotary film evaporator.

The oily residue (130 g) was dissolved in chloroform to give 190 ml and this was applied to a column of Merck 7734 silica 60 (200×4 cm) packed in chloroform. The column was washed with chloroform (500 ml) and eluted with chloroform:ethyl acetate (3:1) and fractions of approximately 40 ml were collected after a forerun of 1,400 ml.

Fractions 32–46 were combined and evaporated to yield an oil (21.2 g). Fractions 47–93 were combined and evaporated to give an oil (20.1 g) which was dissolved in chloroform:ethyl acetate (3:1) to 50 ml, and applied to a column of Merck 7734 silica 60 (200×4 cm) packed in chloroform:ethyl acetate (3:1), and fractions of approximately 40 mls were collected after a forerun of 1,400 ml. Fractions 22–36 were combined and evaporated to give an oil (3.1 g) which was added to the oil obtained from fractions 32–46 from the first column. The combined oils were dissolved in boiling methanol (4 ml) which was then added to hot propan-2-ol (20 ml) and allowed to crystallise.

Mother liquor after crystallisation was evaporated to yield an oil which was dissolved in an equal volume of methylene chloride and loaded onto a column (30×2.2 cm) of Merck Kieselgel 60 (70-230 mesh ASTM, Art. No. 7734) packed in methylene chloride. The bed was washed with methylene chloride (2 bed volumes) and eluted with chloroform:ethyl acetate (3:1) (2 bed volumes). Evaporation of the eluate yielded an oil which was dissolved in methanol and subjected to preparative high performance liquid chromatography (hplc) on Spherisorb S5 ODS-2 (250 mm×20 mm, Phase Sep. Ltd.). Portions of the sample (5 ml) were pumped onto the column over a period of 1 minute and the column was eluted with acetonitrile:water (7:3) under the following conditions:

| Time (mins) | Flow (ml/min) | |
|---|---|---|
| 0.00 | 0.00 | ⎫ Injection |
| 1.00 | 0.00 | ⎭ time |
| 1.10 | 30.00 | |
| 39.90 | 30.00 | |
| 40.00 | 35.00 | |
| 75.00 | 35.00 | |

Material eluting from the hplc column was monitored by uv spectroscopy at 238 nm.

Evaporation of the combined fractions with peaks eluting at 33.4 minutes yielded the *title compound* (34 mg) as a solid.

E.I. mass spectroscopy yielded a molecular ion at 610 and gave characteristic fragments at: 592, 574, 556, 422, 259, 241.

EXAMPLE 1

23[E]-Methoxyimino Factor A (a) 5,23-Diketo Factor A

An ice-cold solution prepared from concentrated sulphuric acid (1.2 ml) and sodium dichromate (120 mg) in water (2 ml) was added over 15 min to an ice-cold solution of 5-keto Factor A (200 mg) and tetrabutylammonium hydrogen sulphate (15 mg) in ethyl acetate (4 ml) with vigorous stirring. After 1 h the mixture was diluted with ethyl acetate and the organic phase was washed with saturated aqueous sodium bicarbonate. The dried organic phase was evaporated and the gum was purified by chromatography over Merck Keiselgel 60 230-400 mesh (100 ml). Elution with 10% ethyl acetate in dichloromethane afforded the *title compound* as a pale yellow foam (86 mg) δ (CDCl$_3$) includes 6.57 (m, 1H); 2.50 (s, 2H); and 1.89 (m, 3H).

(b) 5-Keto, 23[E]-methoxyimino Factor A 5,23-Diketo Factor A (475 mg), methoxylamine hydrochloride (69 mg) and anhydrous sodium acetate (135 mg) were dissolved in methanol. After 1.5 h at room temperature, the solution was kept at −18° for 16 h, diluted with ethyl acetate and washed successively with 1N hydrochloric acid, water, and brine. The dried organic phase was evaporated and the yellow foam was purified by chromatography over Merck Keiselgel 60, 230-400 mesh (120 ml). Elution of the column with hexane:ethyl acetate (4:1) afforded the *title compound* as a yellow foam (255 mg) $[\alpha]_D^{21}+80°$ (c 1.20, CHCl$_3$), λ$_{max}$ (EtOH) 241 nm (ε 27,500), ν$_{max}$ (CHBr$_3$), 3530, 3460 (OH) 1708 (C=O), 1676 (C=C—C=O), 986 (C—O), δ (CDCl$_3$) includes 6.58 (s; 1H), 3.84 (s; 4H), 3.80 (s; 1H), 3.58 (m; 1H), 3.30 (d14; 1H), 1.00 (d6; 3H), 0.96 (d6; 3H), 0.92 (d6; 3H).

(c) 23[E]-Methoxyimino Factor A (i) Sodium borohydride (6.5 mg) was added to an ice-cold solution of 5-keto, 23[E]-methoxyimino Factor A (83 mg) in isopropanol (20 ml). The yellow mixture was stirred for 35 min in an ice-bath, diluted with ethyl acetate and washed successively with 1N hydrochloric acid, water and brine. The dried organic phase was evaporated and the resultant yellow gum was purified by chromatography over Merck Keiselgel 60, 230-400 mesh (60 ml). Elution of the column with hexane:ethyl acetate (2:1) afforded the *title compound* as a yellow foam (58 mg). Crystallisation from hexane afforded the *title compound*, m.p. 203°, $[\alpha]_D^{21}+133°$ (c 1.12, CHCl$_3$), λ$_{max}$ (EtOH) 244 nm (ε 26,200), δ (CDCl$_3$) includes 4.29 (t7; 1H), 3.84 (s; 3H), 3.29 (d15; 1H).

(ii) A solution of 5-keto, 23[E]-methoxyimino Factor A (50 mg) in dry tetrahydrofuran (1 ml) was added to a cooled (−78°) solution of lithium tris-t-butoxyaluminium hydride (261 mg) in dry tetrahydrofuran (3 ml). After 0.75 h at −78°, the solution was diluted with ethyl acetate (30 ml) and washed successively with 0.5N hydrochloric acid and water. The dried organic phase was evaporated and the crude product was purified by chromatography over Merck Kieselgel 60, 230-400 mesh (40 ml), eluting with 25% ethyl acetate in hexane to afford the *title compound* as a white foam, $[\alpha]_D^{21}+128°$ (c 0.95, CHCl$_3$), δ(CDCl$_3$) includes 4.29 (t7; 1H), 3.84(s; 3H), 3.29(d15; 1H).

EXAMPLE 2

23[E]-Methoxyimino Factor A, 5-acetate

A solution of anhydrous sodium acetate (2.8 g) in water (15 ml) was added to a solution of 23-keto Factor A, 5-acetate (3.13 g, Example 18 in UK Patent Specification 2176182) in methanol, followed by methoxyamine hydrochloride (3.01 g). The resultant solution was stirred for 1.5 h at 20°, diluted with ethyl acetate then washed successively with 0.5N hydrochloric acid, water and brine. The dried organic phase was evaporated to near dryness and the off-white foam was purified by chromatography over Merck Kieselgel 60 230-400 mesh (600 ml). Elution of the column with hexane:ethyl acetate (4:1) afforded the *title compound* as a colourless foam (2.14 g) $[\alpha]_D^{21}+128°$ (C 1.35, CHCl$_3$) λ$_{max}$ (EtOH) 244 nm (ε$_{max}$ 27,250); ν$_{max}$ (CHBr$_3$) 3560, 3480 (OH), 1733 (acetate), 1715 (C=O), 995 (C—O), δ(CDCl$_3$) include 5.5–5.6 (m: 2H), 3.84 (S: 3H) 3.29 (d 15; H), 2.16 (S: 3H).

EXAMPLE 3

23[E]-Hydroxyimino Factor A, 5-acetate

Reaction of 23-keto Factor A, 5-acetate with hydroxylamine hydrochloride was effected in a manner similar to that described in Example 1 above. The crude product was purified by chromatography over Merck Kieselgel 60 230-400 mesh, eluting with ethyl acetate:acetonitrile (4:1) to afford the *title compound* as a colourless foam $[\alpha]_D^{21}+132°$ (c 1.01, CHCl$_3$), λ$_{max}$ (EtOH) 244 nm (ε$_{max}$ 27800), ν$_{max}$ (CHBr$_3$) 3565, 3470 (OH), 1732 (acetate), 1712 (C=O), 993 (C—O), δ(CDCl$_3$) include 8.12 (S; 1H), 5.5–5.6 (m: 2H), 3.42 (d 15: 1H), 2.16 (S: 3H).

EXAMPLE 4

23[E]-Methoxyimino Factor A

A solution of the product of Example 2 (1.88 g) in methanol was cooled in an ice bath, 1N aqueous sodium hydroxide (5.6 ml) was added, and the solution was stirred in an ice bath for 1.5 h. The solution was diluted with ethyl acetate and washed successively with 0.5N aqueous hydrochloride acid, water and brine. The dried organic phase was evaporated and the resultant foam was purified by chromatography over Merck Kieselgel 60 230-400 mesh (400 ml). Elution of the column with hexane:ethyl acetate (2:1) afforded a colourless foam (1.429 g) Crystallisation from hexane afforded the pure *title compound*, m.p. 203°, $[\alpha]_D^{21}+132°$ (c 1.21, CHCl$_3$), $\lambda_{max}$ (EtOH) 244 nm ($\epsilon_{max}$ 29200), $\nu_{max}$ (CHBr$_3$) 3540 (OH), 1708 (C=O), 992 (C—O), $\delta$(CDCl$_3$) includes 4.29 (t7: 1H), 3.84 (s: 3H), 3.29 (d15: 1H).

EXAMPLE 5

23[E]-Hydroxyimino Factor A

Hydrolysis of the product of Example 3 according to the method described in Example 3 above gave a product which was purified by chromatography over Merck Kieselgel 60 230-400 mesh (400 ml) eluting with hexane:ethyl acetate (1:1) to afford the *title compound* as a colourless foam $[\alpha]_D^{21}+140°$ (c 1.24, CHCl$_3$), $\lambda_{max}$ (EtOH) 244 nm ($\epsilon_{max}$ 26700) $\nu_{max}$ (CHBr$_3$) 3565, 3490 (OH), 1710 (C=O), 994 (C—O), $\delta$(CDCl$_3$) include 8.11 (S: 1H), 4.29 (t7: 1H), 3.41 (d15: 1H).

EXAMPLE 6

23[E]-Ethoxyimino Factor A

A solution of anhydrous sodium acetate (140 mg) in water (3 ml) was added to a solution of 23-keto Factor A (200 mg, Example 23 in UK Patent Specification 2176182) and ethoxyamine hydrochloride (126 mg) in methanol (20 ml). After 2 h at 20° the solution was diluted with ether (40 ml) and washed with water. The dried organic phase was evaporated and the resultant off white foam was purified by chromatography over Merck Kieselgel 60 230-400 mesh (90 ml). Elution of the column with hexane:ethyl acetate (2:1) afforded the *title compound* as a colourless foam (189 mg) $[\alpha]_D^{21}+125°$ (c 1.00, CHCl$_3$) $\lambda_{max}$ (EtOH) 244 nm ($\epsilon_{max}$ 28,200), $\nu_{max}$ (CHBr$_3$) 3540, 3480 (OH), 1705 (C=O), 990 (C—O), $\delta$(CDCl$_3$) include 4.30 (t7: 1H), 4.10 (q7: 2H), 3.31 (d15: 1H), 1.24 (t7: 3H).

The compounds of Examples 7, 8 and 9 were prepared in a similar manner from 23-keto Factor A and the appropriate alkoxyamine.

EXAMPLE 7

23[E]-Allyloxyimino Factor A $[\alpha]_D^{21}+124°$ (c 1.16, CHCl$_3$), $\lambda_{max}$ (EtOH) 244 nm ($\epsilon_{max}$ 28,400), $\nu_{max}$ (CHBr$_3$) 3550, 3490 (OH), 1708 (C=O), 990 (C—O), $\delta$(CDCl$_3$) include 5.98 (m; 1H), 5.28 (dd17, 2; 1H), 5.15 (dd9, 2; 1H), 4.5–4.7 (m; 2H), 4.29 (t7; 1H), 3.36 (d14; 1H) was prepared from allyloxyamine hydrochloride.

EXAMPLE 8

23[E]-Isopropyloxyimino Factor A $[\alpha]_D^{21}+116°$ (c 0.97, CHCl$_3$), $\lambda_{max}$ (EtOH) 244 nm ($\epsilon_{max}$ 25,000), $\nu_{max}$ (CHBr$_3$) 3550, 3490 (OH), 1708 (C=O), 992 (C—O), $\delta$(CDCl$_3$) include 4.2–4.4 (m;2H), 3.30 (d14;1H), 1.21 (d7;3H), 1.20 (d7;3H) was prepared from isopropyloxyamine hydrochloride.

EXAMPLE 9

23[E]-n-Butoxyimino Factor A $[\alpha]_D^{21}+115°$ (c 1.10, CHCl$_3$), $\lambda_{max}$ (EtOH) 244 nm ($\epsilon_{max}$ 31,800), $\nu_{max}$ (CHBr$_3$) 3540, 3460, (OH), 1708 (C=O), 992 (C—O), $\delta$(CDCl$_3$) include 4.28 (t6;1H), 4.03 (m;2H), 3.96 (d6;1H), 3.31 (d14;1H), 0.9–1.1 (m;15H) was prepared from n-butoxyamine hydrochloride.

EXAMPLE 10

23[E]-Methoxyimino Factor A,5-acetate (1) A 3-molar solution of methylmagnesium iodide in ether (0.16 ml) was added to a stirred solution of the product of Example 3 (120 mg) in dry hexamethylphosphoric triamide (5 ml) under nitrogen. Iodomethane (0.09 ml) was added, and after 1 h, the mixture was diluted with ethyl acetate (30 ml) and washed successively with 2N hydrochloric acid and water. The dried organic phase was evaporated and the yellow gum was purified by chromatography over Merck Kieselgel 60 230-400 mesh (80 ml). Elution of the column with hexane:ethyl acetate (2:1) afforded the title compound as a white foam $[\alpha]_D^{21}+123°$ (c 1.25, CHCl$_3$) $\lambda_{max}$ (EtOH) 245 nm ($\epsilon_{max}$ 30,300). NMR was as described above in Example 2.

(ii) The product of Example 3 (0.082 g) was dissolved in diethyl ether (10 ml) containing silver oxide (0.4 g), freshly prepared form aqueous silver nitrate and 2M sodium hydroxide). The mixture was stirred at room temperature for 2h, whereupon it was filtered and the solvent evaporated to yield a crude yellow gum, This residue was purified by preparative thin layer chromatography (Merck 5717) eluting with dichloromethane/acetone (25:1). The main band was extracted with acetone and evaporated to yield the title compound (0.059 g) NMR was described above in Example 2.

EXAMPLE 11

23[E]-Methoxyimino Factor A,5-methylcarbamate

Methyl isocyanate (0.13 ml, 125 mg) and triethylamine (2 drops) were added to a solution of 23[E]-methoxyimino Factor A (350 mg) in dry dimethylformamide (0.75 ml). The flask was stoppered and heated for 5.5 h at 80° with stirring. The reaction mixture was poured into water (50 ml) and the resulting mixture was filtered through kieselguhr. The filter cake was washed with water (150 ml) and then extracted with dichloromethane (75 ml). The extract was dried (MgSO$_4$) and concentrated to give a yellow foam which was purified by medium pressure column chromatography on silica (125 g, Merck Kieselgel 60, 230-400 mesh). Elution with hexane:ethyl acetate (1:1) gave the title compound as a white foam (206 mg). $[\alpha]_D^{22}+99°$ (c 0.55, CH$_2$Cl$_2$); $\lambda_{max}$ (EtOH) 244.4 nm ($\epsilon$ 28710); $\nu_{max}$ (CHBr$_3$) 3530 (OH), 3455 (NH), 1720 (ester), 1720+1510 (carbamate) and 993 cm$^{-1}$ (C—O); $\delta$ (CDCl$_3$) includes 1.78 (s, 3H), 2.86 (d, 5 Hz, 3H), 3.29 (d, 14 Hz, 1H), 3.83 (s, 3H), 4.80 (q, 5 Hz, 1H) and 5.50 (m, 2H).

EXAMPLE 12

23[E]-Methoxyimino Factor A,5-methylcarbonate

To a solution of 23[E]-methoxyimino Factor A (150 mg) in dichloromethane (15 ml) and pyridine (0.3 ml) stirring at 0° was added methylchloroformate (0.7 ml of 1.0M solution in dichloromethane). The reaction mixture was left stirring at 0°-3° for 20 min., then was added to dichloromethane (70 ml) and washed with 2N hydrochloric acid (50 ml) and water (50 ml). The organic phase was dried (MgSO$_4$) and solvent removed to give a foam which was purified by medium pressure column chromatography on silica (40 g, Merck kieselgel 60, 230-400 mesh). Elution with dichloromethane:ethyl acetate (30:1) gave the *title compound* as a white foam (127 mg). $[\alpha]_D^{21}+145°$ (c=0.41, CH$_2$Cl$_2$);

$\lambda_{max}$ (EtOH) 244.4 nm ($\epsilon$ 31210); $\nu_{max}$ (CHBr$_3$) 3460+3540 (OH), 1742 (carbonate) 1710 (ester) and 992 cm$^{-1}$ (C—O); $\delta$ (CDCl$_3$) includes 1.82 (s, 3H), 3.29 (d 14 Hz, 1H), 3.82 (s, 3H), 3,83 (s, 3H), 5.2–5.4 (m; 3H) 5.56 (s, 1H).

EXAMPLE 13

23[E]-Methoxyimino Factor D,5-acetate

A solution containing 23-keto Factor D,5-acetate (251 mg, Example 119 in UK Patent Specification 2176182), sodium acetate (250 mg) and methoxyamine hydrochloride (250 mg) in methanol (40 ml) was kept at 20° for 24 h, concentrated to ca 10 ml, diluted with ethyl acetate (50 ml), and washed successively with 0.5N hydrochloric acid and water. The dried organic phase was evaporated to afford a yellow foam which was purified by chromatography over Merck Keiselgel 60, 230–400 mesh (120 ml). Elution of the column with hexane afford the *title compound* as a pale yellow foam (144 mg);

$\lambda_{max}$ (EtOH) 244 nm ($\epsilon$ 26,400); $\nu_{max}$ (CHBr$_3$) (cm$^{-1}$) 3500 (OH), 1732 (OAc), 1710 (C=O); $\delta$ (CDCl$_3$) include 5.54 (m; 2H), 4.92 (m; 1H), 3.84 (s; 3H), 3.32 (m; 1H), 3.30 (d14; 1H), 2.17 (s; 3H), 1.91 (d14; 1H), 1.76 (s; 3H), 1.63 (s; 3H), 1.51 (s; 3H), 1.01 (t7,; 3H), 0.99 d6; 3H), 0.92 (d6; 3H).

EXAMPLE 14

23[E]-Methoxyimino Factor D

A solution containing the product of Example 13 (140 mg) and 1N sodium hydroxide (0.6 ml) in methanol (8 ml) was stirred in an ice bath for 1.5 h. The solution was diluted with ethyl acetate (30 ml) and washed successively with 1N hydrochloride acid and water. The dried organic phase was evaporated to afford a yellow foam which was purified by chromatography over Merck Keiselgel 60, 230–400 mesh (50 ml). Elution of the column with hexane:ethyl acetate (2:1) afforded the title compound as an off-white foam (105 mg); $[\alpha]_D^{21}+96°$ (c 1.38, CHCl$_3$); $\lambda_{max}$ (EtOH) 244 nm ($\epsilon$ 26,700); $\nu_{max}$ (CHBr$_3$) (cm$^{-1}$) 3550, 3500 (OH), 1710 (C=O); $\delta$ (CDCl$_3$) include 4.93 (m; 1H), 4.30 (t6; 1H), 3.95 (d6; 1H), 3.84 (s; 3H), 3.30 (d14; 1H), 3.27 (m; 1H), 1.88 (s; 3H), 1.64 (s; 3H), 1.52 (s; 3H), 1.01 (t7; 3H), 1.00 (d6; 3H), 0.92 (d6; 3H).

EXAMPLE 15

23[E]-Methoxyimino Factor B

A solution containing 23-keto Factor B (1 g, Example 19 in UK Patent Specification 2176182), sodium acetate (400 mg) and methoxyamine hydrochloride (400 mg) was stirred at 20° for 20 h, concentrated to ca 10 ml diluted with ethyl acetate, and washed with water. The organic phase was washed successively with 0.5N hydrochloric acid and water, and the dried organic phase was evaporated and the crude product was purified by chromatography over Merck Keiselgel 60, 230–400 mesh (200 ml). Elution of the column with ethyl acetate:dichloromethane (1:9) afforded the *title compound* as a white foam (500 mg); $[\alpha]_D^{21}+128°$ (c 1.09, CHCl$_3$); $\lambda_{max}$ (EtOH) 244 nm ($\epsilon$ 30,100); $\nu_{max}$ (CHBr$_3$) (cm$^{-1}$) 3540, 3460 (OH), 1708 (c=O); $\delta$ (CDCl$_3$) include 5.46 (q6; 1H), 4.03 (d5; 1H), 3.97 (d5; 1H), 3.83 (s; 3H), 3.50 (s; 3H), 3.32 (m; 1H), 3.29 (d14; 1H), 1.82 (s; 3H), 1.68 (d6; 3H), 1.00 (d6; 3H), 0.92 (d6; 3H).

EXAMPLE 16

23[E]-Methoxyimino Factor C

Anhydrous sodium acetate (0.54 g) and methoxyamine hydrochloride (0.58 g) were added to a solution of 23-keto Factor C (1.97 g, Example 12 in UK Patent Specification 2176182) in methanol (30 ml) containing water (5 ml) and the mixture was stirred for 30 min at room temperature. Ethyl acetate (30 ml) and 0.5M hydrochloric acid (30 ml) were added and the aqueous layer re-extracted with ethyl acetate (15 ml). The combined organic layers were washed in turn with 0.5M hydrochloric acid, 5% saturated aq. sodium bicarbonate and 10% saturated aq. sodium chloride, then concentrated in vacuo to a yellow foam which was purified by chromatography on Merck 9385 silica gel initially developing the column with dichloromethane and then eluting with dichloromethane containing a small amount of ethyl acetate (up to 10%) to give the *title compound* (1.0 g); $[\alpha]_D^{21}+64°$ (C1.0, CH$_3$OH); $^1$H NMR (CDCl$_3$) includes the following signals: $\delta$4.95 (m, 1H); 4.29 (t, 1H, 7 Hz); 3.96 (d, 1H, 7 Hz); 3.85 (s, 3H [=NOCH$_3$]); 3.66 (d, 1H, 10 Hz); 1.51 (s, 3H); 1.42 (t, 1H, 12 Hz); IR (CHBr$_3$) 3620–3340 cm$^{-1}$ (—OH), 1711 cm$^{-1}$(C=O).

The following are examples of formulations according to the invention. The term 'Active Ingredient' as used hereinafter means a compound of the invention and may be for example the compound of Example 4.

Multidose parenteral injection

| Multidose parenteral injection | | |
| --- | --- | --- |
| Example 1 | % w/v | Range |
| Active ingredient | 2.0 | 0.1–6.0% w/v |
| Benzyl alcohol | 1.0 | |
| Polysorbate 80 | 10.0 | |
| Glycerol formal | 50.0 | |
| Water for Injections to | 100.0 | |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

| Example 2 | % w/v | Range |
| --- | --- | --- |
| Active ingredient | 4.0 | 0.1–7.5% w/v |
| Benzyl alcohol | 2.0 | |
| Glyceryl triacetate | 30.0 | |
| Propylene glycol to | 100.0 | |

Dissolve the active ingredient in the benzyl alcohol and glyceryl triacetate. Add the propylene glycol and make up to volume. Sterilize the product by conventional pharmaceutical methods, for example sterile filtration, and package aseptically.

| Example 3 | % | Range |
| --- | --- | --- |
| Active ingredient | 2.0 w/v | 0.1–.5% w/v |
| Ethanol | 36.0 v/v | |
| Non-ionic surfactant (e.g. Synperonic PE L44*) | 10.0 w/v | |
| Propylene glycol to | 100.0 | |

*Trademark of ICI

Dissolve the active ingredient in the ethanol and surfactant and make up to volume. Sterilize the product by conventional pharmaceutical methods, for example sterile filtration, and package aseptically.

| Example 4 | % | Range |
| --- | --- | --- |
| Active Ingredient | 2.0 w/v | 0.1–3.0% w/v |
| Non-ionic surfactant | | |
| (e.g. Synperonic PE F68*) | 2.0 w/v | |
| Benzyl alcohol | 1.0 w/v | |
| Miglyol 840** | 16.0 v/v | |
| Water for Injections to | 100.0 | |

*Trademark of ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

| Aerosol spray | % w/w | Range |
| --- | --- | --- |
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet Method of manufacture - wet granulation | |
| --- | --- |
| | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose to tablet core weight of | 450 mg |

Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use Method of manufacture - dry granulation | |
| --- | --- |
| | mg |
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

| Veterinary intrammary injection | | mg/dose | Range |
| --- | --- | --- | --- |
| Active Ingredient | | 150 mg | 0.05–1.0 g |
| Polysorbate 60 | 3.0% w/w | | |
| White Beeswax | 6.0% w/w | to 3 g | to 3 or 15 g |
| Arachis oil | 91.0% w/w | | |

Heat the arachis oil, white beeswax and polysorbate 60 to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary slow-release bolus | % w/w | Range |
| --- | --- | --- |
| Active Ingredient | | 0.25–2 g |
| Colloidal silicon dioxide | 2.0 | to required fill weight |
| Microcrystalline cellulose to | 100.0 | |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient.

| Veterinary oral drench | % w/v | Range |
| --- | --- | --- |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer as | pH 6.0–6.5 | |
| Water to | 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | % w/w | Range |
| --- | --- | --- |
| Active Ingredient | 4.0 | 1–20% w/w |
| Saccharin sodium | 2.5 | |
| Polysorbate 85 | 3.0 | |
| Aluminum distearate | 5.0 | |
| Fractionated coconut oil to | 100.0 | |

Disperse the aluminium distearate in the fractionated coconut oil and polysorbate 85 by heating. Cool to room temperature and disperse the saccharin sodium in the oily vehicle. Disperse the active ingredient in the base. Fill into plastic syringes.

| Granules for the veterinary in-feed administration | % w/w | Range |
|---|---|---|
| Active Ingredient | 2.5 | 0.05–5% w/w |
| Calcium sulphate, hemi-hydrate to | 100.0 | |

Blend the Active Ingredient with the calcium sulphate. Prepare the granules using a wet granulation process. Dry using a tray or fluid-bed drier. Fill into the appropriate container.

| Veterinary Pour-on | % w/v | Range |
|---|---|---|
| Active Ingredient | 2.0 | 0.1 to 30% |
| Dimethyl sulphoxide | 10.0 | |
| Methyl Isobutyl ketone | 30.0 | |
| Propylene glycol (and pigment) to | 100.0 | |

Dissolve the active ingredient in the dimethyl sulphoxide and the methyl isobutyl ketone. Add the pigment and make up to volume with the propylene glycol. Fill into the pour-on container.

| Emulsifiable Concentrate | |
|---|---|
| Active ingredient | 50 g |
| Anionic emulsifier (e.g. Phenyl sulphonate CALX) | 40 g |
| Non-ionic emulsifier (e.g. Synperonic NP13)* | 60 g |
| Aromatic solvent (e.g. Solvesso 100) to | 1 liter. |

*Trademark of ICI

Mix all ingredients, stir until dissolved.

| Granules | | |
|---|---|---|
| (a) | Active ingredient | 50 g |
| | Wood resin | 40 g |
| | Gypsum granules (20–60 mesh) to (e.g. Agsorb 100A) | 1 kg |
| (b) | Active ingredient | 50 g |
| | Synperonic NP13* | 40 g |
| | Gypsum granules (20–60 mesh) to | 1 kg. |

*Trademark of ICI

Dissolve all ingredients in a volatile solvent e.g. methylene chloride, add to granules tumbling in mixer. Dry to remove solvent.

The pesticidal activity of the compounds of the invention was determined using a variety of pests and their hosts according to the following general procedure:

The product was used in the form of a liquid preparation. The preparations were made by dissolving the product in acetone. The solutions were then diluted with water containing 0.1% or 0.01% by weight of a wetting agent until the liquid preparations contained the required concentration of the product.

The test procedure adopted with regard to most pests comprised supporting a number of the pests on a medium which was usually a host plant and either treating the medium with the preparation (residual test) or in the case of *Tetranychus urticae, Myzus persicae, Nilaparvata lugens* and *Musca domestica,* both the pests and the medium were treated with the preparation (contact test). In the case of *Meloidogyne incognita* the solution was applied to soil in which tomato plants were growing, subsequently treated with nematodes and the reduction in the number of root-knots assessed in comparison with a control plant.

Following these procedures, the compound of formula (I) in which $R^1$ is isopropyl, $R^2$ is methyl and $R^3$ is hydrogen was found to be effective at concentrations (by weight of product) of 100 parts per million or less.

We claim:

1. A compound of formula (I)

or a salt thereof, wherein $R^1$ represents a methyl, ethyl or isopropyl group;

$R^2$ represents a hydrogen atom, a $C_{1-8}$ alkyl group or a $C_{3-8}$ alkenyl group and the group $=NOR^2$ is in the E-configuration;

$OR^3$ is a substituted hydroxy group which has a formula $-OCSOR^4$, where $R^4$ is an aliphatic, araliphatic, or aromatic group;

a group $-OSO_2R^6$, where $R^6$ is $C_{1-4}$alkyl or $C_{6-10}$aryl;

a group $OCO(CH_2)_nCO_2R^7$ where $R^7$ is a hydrogen atom or an aliphatic, araliphatic or aromatic group, and n represents 0, 1 or 2;

or a group $OCONR^8R^9$, where $R^8$ and $R^9$ may each independently represent a hydrogen atom or a $C_{1-4}$ alkyl group.

2. A compound according to claim 1 in which $R^1$ is an isopropyl group.

3. A compound according to claim 1 in which $R^2$ is a methyl group.

4. A pharmaceutical composition containing a pesticidally effective amount of at least one compound according to claim 1 together with a pharmaceutically acceptable carrier.

5. A veterinary composition containing a pesticidally effective amount of at least one compound according to claim 1 together with a veterinarian carrier.

6. A pesticidal composition containing a pesticidally effective amount of at least one compound according to claim 1 together with a carrier.

7. A composition as claimed in claim 4 containing an effective amount of the compound wherein $R^1$ is an isopropyl group and $R^2$ is a methyl group.

8. A method for combatting pests in agriculture, horticulture or forestry or in other locations of the pests which comprises applying to plants, vegetation, the pest themselves a pesticidally effective amount of a compound according to claim 1.

9. A method as claimed in claim 8 in which said pests are insect, acarine or nematode pests.

10. A method for treating endoparasitic, ectoparasitic or fungal conditions in animals and humans which comprises administering to the animal or patient an effective amount of one or more compounds according to claim 1.

11. A method for treating endoparasitic or ectoparasitic conditions in animals an humans which comprises administering to the animal or patient an effective amount of one or more compounds according to claim 1.

12. A method for treating endoparasitic or ectoparasitic conditions in animals which comprises administering to the animal an effective amount of one or more compounds according to claim 1.

13. A method for treating endoparasitic or ectoparasitic conditions in animals which comprises administering to the animal an effective amount of the compound according to claim 8.

* * * * *